United States Patent [19]

Beavis et al.

[11] Patent Number: 5,453,247
[45] Date of Patent: Sep. 26, 1995

[54] INSTRUMENT AND METHOD FOR THE SEQUENCING OF GENOME

[75] Inventors: Ronald C. Beavis, St. John's, Canada; Brian T. Chait, New York, N.Y.

[73] Assignee: The Rockefeller University, New York, N.Y.

[21] Appl. No.: 156,316

[22] Filed: Nov. 23, 1993

Related U.S. Application Data

[63] Continuation of Ser. No. 957,688, Oct. 7, 1992, Pat. No. 5,288,644, which is a continuation of Ser. No. 504,643, Apr. 4, 1990, abandoned.

[51] Int. Cl.$^6$ .......................... G01N 33/00; G01N 24/00
[52] U.S. Cl. ..................... 422/68.1; 436/173; 435/291; 935/87; 935/88
[58] Field of Search .................. 422/62, 67, 82.05, 422/68.1; 436/173; 435/6, 291; 536/27–29; 935/87, 88

[56] References Cited

U.S. PATENT DOCUMENTS

| | | | |
|---|---|---|---|
| 4,702,808 | 10/1987 | Lemelson | 204/157.41 |
| 4,705,616 | 11/1987 | Andresen et al. | 204/299 R |
| 5,003,059 | 3/1991 | Brennan | 536/27 |
| 5,210,412 | 5/1993 | Levis et al. | 250/288 |
| 5,221,518 | 6/1993 | Mills | 422/62 |

OTHER PUBLICATIONS

Barber et al. "Fast atom bombardment of solids as an ion source in mass spectrometry" Nature vol. 293 24 Sep. 1981.

*Primary Examiner*—David A. Redding
*Attorney, Agent, or Firm*—Browning, Bushman, Anderson & Brookhart

[57] ABSTRACT

Improved techniques are provided for DNA sequencing, and particularly for sequencing of the entire human genome. Different base-specific reactions are utilized to use different sets of DNA fragments from a piece of DNA of unknown sequence. Each of the different sets of DNA fragments has a common origin and terminates at a particular base along the unknown sequence. The molecular weight of the DNA fragments in each of the different sets is detected by a matrix assisted laser absorption mass spectrometer to determine the sequence of the different bases in the DNA. The methods and apparatus of the present invention provide a relatively simple and low cost technique which may be automated to sequence thousands of gene bases per hour, and eliminates the tedious and time consuming gel electrophoresis separation technique conventionally used to determine the masses of DNA fragments.

20 Claims, 2 Drawing Sheets

INSTRUMENT AND METHOD FOR THE SEQUENCING OF GENOME

This is a continuation of application Ser. No. 07/957,688, filed Oct. 7, 1992, now U.S. Pat. No. 5,288,644, which is a continuation of application Ser. No. 07/504,643, filed Apr. 4, 1990, now abandoned.

BACKGROUND OF THE INVENTION

1. Field of the Invention

The present invention relates to sequencing of DNA and more particularly to the sequencing of the entire human genome.

2. Description of the Background

A human being has 23 pairs of chromosomes consisting of a total of about 100,000 genes. The human genome consists of those genes. A single gene which is defective may cause an inheritable disease, such as Huntington's disease, Tay-Sachs disease or cystic fibrosis. The human chromosomes consist of large organic linear molecules of double-strand DNA (deoxyribonucleic acid) with a total length of about 3.3 billion "base pairs". The base pairs are the chemicals that encode information along DNA. A typical gene may have about 30,000 base pairs. By correlating the inheritance of a "marker" (a distinctive segment of DNA) with the inheritance of a disease, one can find a mutant (abnormal) gene to within one or two million base pairs. This opens the way to clone the DNA segment, test is activity, follow its inheritance, and diagnose carriers and future disease victims.

The mapping of the human genome is to accurately determine the location and composition of each of the 3.3 billion bases. The complexity and large scale of such a mapping has placed it, in terms of cost, effort and scientific potential of such projects, as one of the largest and most important projects of the 1990's and beyond.

The problem of DNA sequence analysis is that of determining the order of the four bases on the DNA strands. The present status of techniques for determining such sequences is described in some detail in an article by Lloyd M. Smith published in the American Biotechnology Laboratory, Volume 7, Number 5, May 1989, pp 10–17. Since the early 1970's, two methods have been developed for the determination of DNA sequence: (1) the enzymatic method, developed by Sanger and Coulson; and (2) the chemical degradation method, developed by Maxam and Gilbert. Both of these techniques are based on similar principals, and employ gel electrophoresis to separate DNA fragments of different lengths with high resolution. On these gels it is thus possible to separate a DNA fragment 600 bases in length from one 601 bases in length.

The two sequencing methods differ in the techniques employed to produce the DNA fragments, but are otherwise similar. In the Maxam-Gilbert method, four different base-specific reactions are performed on portions of the DNA molecules to be sequenced, to produce four sets of radiolabeled DNA fragments. These four fragment sets are each loaded in adjacent lanes of a polyacrylamide slab gel, and are separated by electrophoresis. Autoradiographic imaging of the pattern of the radiolabeled DNA bands in the gel reveals the relative size, corresponding to band mobilities, of the fragments in each lane, and the DNA sequence is deduced from this pattern.

At least one of these two techniques is employed in essentially every laboratory concerned with molecular biology, and together they have been employed to sequence more than 26 million bases of DNA. Currently a skilled biologist can produce about 30,000 bases of finished DNA sequence per year under ideal conditions. With presently available equipment and trained personnel, sequencing the human genome would require about 100 years of total effort if no other sequencing projects were done. While very useful, the present sequencing methods are extremely tedious and expensive, yet require the services of highly skilled scientists. Moreover, these methods utilize hazardous chemicals and radioactive isotopes, which have inhibited their consideration and further development. Large scale sequencing projects, as that of the human genome, thus appear to be impractical using these well-established techniques.

In addition to being slow, the present DNA sequencing techniques involve a large number of cumbersome handling steps which are difficult to automate. Recent improvements include replacing the radioactive labels with fluorescent tags. These developments have improved the speed of the process and have removed some of the tedious manual steps, although present technology continues to employ the relatively slow gel electrophoresis technique for separating the DNA fragments.

Mass Spectrometry is a well known analytical technique which can provide fast and accurate molecular weight information on relatively complex mixtures of organic molecules. Mass spectrometry has historically had neither the sensitivity nor resolution to be useful for analyzing mixtures at high mass. A series of articles in 1988 by Hillenkamp and Karas do suggest that large organic molecules of about 10,000 to 100,000 Daltons may be analyzed in a time of flight mass spectrometer, although resolution at lower molecular weights is not as sharp as conventional magnetic field mass spectrometry. Moreover, the Hillenkamp and Karas technique is very time-consuming, and requires complex and costly instrumentation.

SUMMARY OF THE INVENTION

In accordance with the present invention, there is provided a method and apparatus for determining the sequence of the bases in DNA by measuring the molecular mass of each of the DNA fragments in mixtures prepared by either the Maxam-Gilbert or Sanger-Coulson techniques. The fragments are preferably prepared as in these standard techniques, although the fragments need not be tagged with radioactive tracers. These standard procedures produce from each section of DNA to be sequenced four separate collections of DNA fragments, each set containing fragments terminating at only one or two of the four bases. In the Maxam-Gilbert method, the four separated collections contain fragments terminating at G, both G and A, both C and T, or C positions, respectively. Each of these collections is sequentially loaded into an ultraviolet laser desorption mass spectrometer, and the mass spectrum of each collection is recorded and stored in the memory of a computer. These spectra are recorded under conditions such that essentially no fragmentation occurs in the mass spectrometer, so that the mass of each ion measured corresponds to the molecular weight of one of the DNA fragments in the collection, plus a proton in the positive ion spectrum, and minus a proton in the negative ion spectrum. Spectra obtained from the four spectra are compared using a computer algorithm, and the location of each of the four bases in the sequence is unambiguously determined.

It is also possible, in principle, to obtain the DNA sequence from a single mass spectrum obtained from a more complex single mixture containing all possible fragments, but both the resolution and mass accuracy required are much higher than in the preferred method described above. As a result the accuracy of the DNA sequence obtained from the single spectrum method will generally be inferior, and the gain in raw sequence speed will be counterbalanced by the need for more repetitions to assure accuracy of the sequence.

The DNA fragments to be analyzed are dissolved in a liquid solvent containing a matrix material. Each sample is radiated with a UV laser beam at a wavelength of between 260 nm to 560 nm, and pulses of from 1 to 20 ns pulsewidth.

It is an objective of the present invention to provide a method and apparatus for the rapid and accurate sequencing of human genome and other DNA material.

It is a further objective of the present invention to provide an instrument and method which are relatively simple to operate, relatively low in cost, and which may be automated to sequence thousands of gene bases per hour.

It is a further objective of the present invention to obtain much faster and more accurate DNA sequence data by eliminating the gel electrophoresis separation technique used in conventional DNA sequencing methods to determine the masses of the DNA fragments in a mixture.

These and further objects of the present invention will become apparent from the following detailed description, wherein reference is made to the figures in the accompanying drawings.

DETAILED DESCRIPTION OF PREFERRED EMBODIMENTS

1. Production of the DNA Fragments

Figure 1:
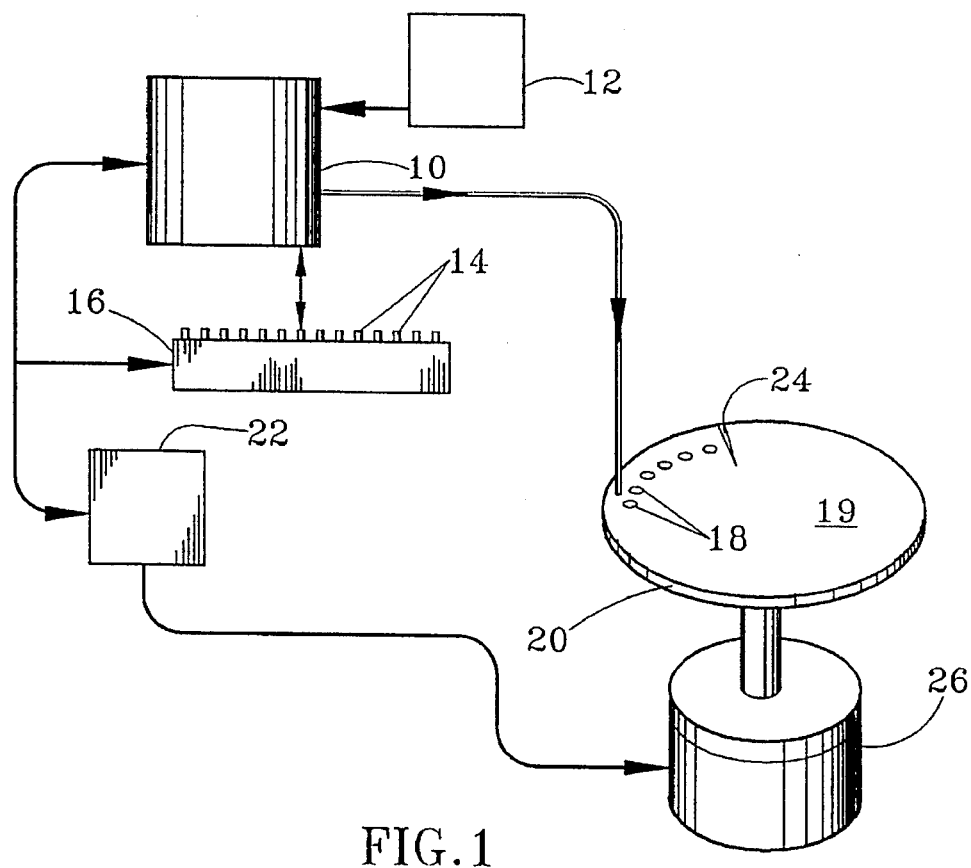
FIG. 1 is a schematic diagram of a technique for depositing DNA fragments from a plurality of samples onto a disk.

The DNA fragments are preferably prepared according to either the enzymatic or chemical degradation sequencing techniques previously described, but the fragments are not tagged with radioactive tracers. These standard procedures produce, from each section of DNA to be sequenced, four separate collections of DNA fragments, each set containing fragments terminating at only one of the four bases. These four samples, suitably identified, are provided as a few microliters of liquid solution.

2. Sample Preparation and Introduction

To obtain intact molecular ions from large molecules, such as DNA fragments, by UV laser desorption mass spectrometry, the samples should be dispersed in a solid matrix that strongly absorbs light at the laser wavelength. Suitable matrices for this purpose include cinnamic acid derivatives such as (4-hydroxy, 3-methoxy) cinnamic acid (ferulic acid), (3,4-dihydroxy) cinnamic acid (caffeic acid) and (3,5-dimethoxy, 4-hydroxy) cinnamic acid (sinapinic acid). These materials may be dissolved in a suitable solvent such as 3:2 mixture of 0.1% aqueous trifluoroacetic acid and acetonitrile at concentrations which are near saturation at room temperature.

One technique for introducing samples into the vacuum of the mass spectrometer is to deposit each sample and matrix as a liquid solution at specific spots on a disk or other media having a planar surface. To prepare a sample for deposit, approximately 1 microliter of the sample solution is mixed with 5–10 microliters of the matrix solution. An aliquot of this mixed solution for each DNA sample is placed on the disk at a specific location or spot, and the volatile solvents are removed by room temperature evaporation. When the solution containing the samples and thousand-fold or more excess of matrix is dried on the disk, the result should be a solid solution of samples each in the matrix at a specific site on the disk.

Each molecule of the sample should be fully encased in matrix molecules and isolated from other sample molecules. Aggregation of sample molecules should not occur. The matrix need not be volatile, but it must be rapidly vaporized following absorption of photons. This can occur as the result of photochemical conversion to more volatile substances. In addition, the matrix must transfer ionization to the sample. To form protonated positive molecular ions from the sample, the proton affinity of the matrix must be less than that of the basic sites on the molecule, and to form deprotonated negative ions, the gas phase acidity of the matrix must be less than that of acidic sites on the sample molecule. Although it is necessary for the matrix to strongly absorb photons at the laser wavelength, it is preferable that the sample does not absorb laser photons to avoid radiation damage and fragmentation of the sample. Therefore, matrices which have absorption bands at longer wavelengths are preferred, such as at 355 nm, since DNA fragment molecules do not absorb at the longer wavelengths.

FIG. 1 depicts a suitable automated DNA sample preparation and loading technique. In this approach, a commercially available autosampler 10 is used to add matrix solution from container 12 to the separated DNA samples. A large number of DNA fragment samples 14, for example 120 samples, may be loaded into a sample tray 16. The matrix solution may be added automatically to each sample 14 using procedures available on such an autosampler 10, and the samples 14 may then be spotted sequentially as sample spots 18 on an appropriate surface, such as the planar surface 19 of the disk 20 rotated by stepper motor 26. Sample spot identification is entered into the data storage and computing system 22 which controls both the autosampler 10 and the mass spectrometer. The location of each spot 18 relative to a reference mark 24 is thus recorded in the computer 22. Sample preparation and loading onto the solid surface 19 is done off-line from the mass spectrometer, and multiple stations may be employed for each mass spectrometer if the time required for sample preparation is longer than the measurement time.

Once the samples in suitable matrix are deposited on the disk, the disk may be inserted into the ion source of a mass spectrometer through the vacuum lock. Any gas introduced in this procedure must be removed prior to measuring the mass spectrum. Loading and pump down of the spectrometer typically requires two to three minutes, and the total time for measurement of each sample to obtain a spectrum is typically one minute or less. Thus 50 or more complete DNA spectrum may be determined per hour according to the present invention. Even if the samples were manually loaded, as disclosed is copending U.S. patent application Ser. No. 07/413,321 filed Sep. 27, 1989 and hereby incorporated by reference, less than one hour would be required to obtain sequence data on a particular segment of DNA, which might be from 400 to 600 bases in length. Even this latter technique is much faster than the conventional DNA sequencing techniques, and compares favorably with the newer automated sequencers using fluorescence labeling. The technique of the present invention does not, however, require the full-time attention of a dedicated, trained operator to prepare and load the samples, and preferably is automated to produce 50 or more spectrum per hour.

Figure 2:
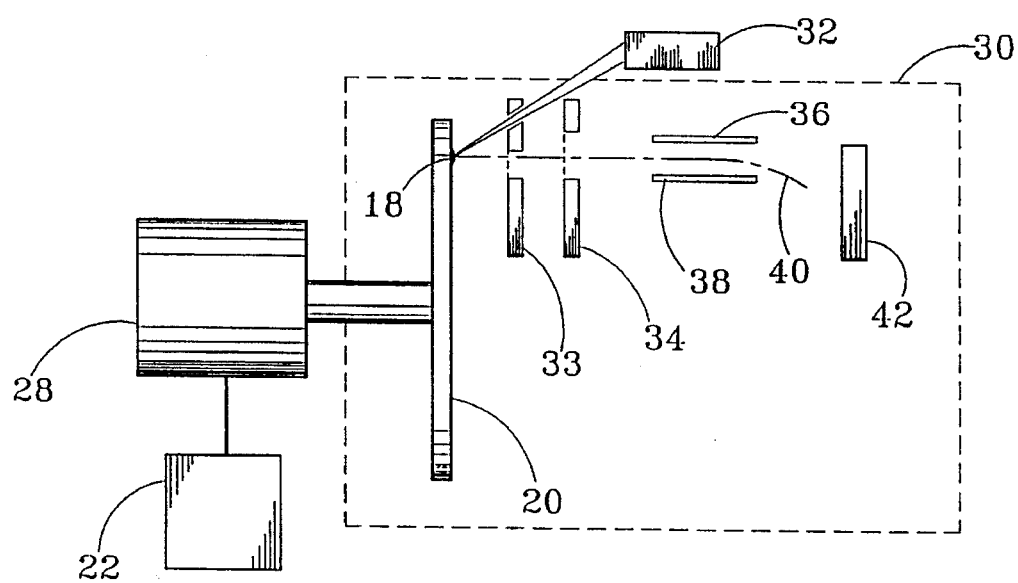
FIG. 2 is a schematic diagram of the laser desorption time-of-flight mass spectrometer with an automated probe assembly for introducing samples into the mass spectrometer.

FIG. 2 depicts in greater detail the preferred technique for DNA sequencing. Under the control of the computer 22, the disk 20 may be rotated by another stepper motor 28 relative to the reference mark 24 to sequentially bring any selected sample 18 to the position for measurement. If the disk contains 120 samples, operator intervention is only required approximately once every two hours to insert a new sample disk, and less than five minutes of each two hour period is required for loading and pumpdown. With this approach, a single operator can service several spectrometers. The particular disk geometry shown for the automated system is chosen for illustrative purposes only. Other geometries, employing for example linear translation of the planar surface, could also be used.

3. The Mass Spectrometer

The present invention preferably utilizes a laser desorption time of flight (TOF) mass spectrometer 30, as generally illustrated in FIG. 2. The disk 20 has a planar face 19 containing a plurality of sample spots 18, each being approximately equal to the laser beam diameter. The disk 20 is maintained at a voltage $V_1$ and may be manually inserted and removed from the spectrometer. Ions are formed by sequentially radiating each spot 18 on the disk 20 with a laser beam from source 32.

The ions extracted from the face 19 of the disk are attracted and pass through the grid covered holes in the metal plates 32, 34, respectively. The plates 32, 34 are at voltages $V_2$ and $V_3$. Preferably $V_3$ is at ground, and $V_1$ and $V_2$ are varied to set the accelerating electrical potential, which typically is in the range of 15,000–50,000 volts. A suitable voltage $V_1$–$V_2$ is 5000 volts and a suitable range of voltages $V_2$–$V_3$ is 10,000 to 45,000 volts.

The low mass ions are almost entirely prevented from reaching the detector 42 by the deflection plates 36, 38. The ions travel as a beam between the deflection plates 36, 38 which suitably are spaced 1 cm. apart and are 3–10 cm long. Plate 36 is at ground and plate 38 receives square wave pulses, for example, at 700 volts with a pulse width in the order of 1 microsecond after the laser strikes the tip. Such pulses suppress the unwanted low mass ions, for example, those under 1,000 Daltons, by deflecting them, as shown by 40, so that the low weight ions do not reach the detector 42, while the higher weight ions pass between the plates 36, 38 after the pulse is off, so they are not deflected, and are detected by detector 42.

An ion detector 42 is positioned at the end of the spectrometer tube and has its front face maintained at voltage $V_d$. The gain of the ion detector 42 is set by $V_d$ which typically is in the range of −1500 to −2500 volts. The detector is a chevron-type tandem microchannel plate array with a front plate at about −2000 volts. The spectrometer tube is straight and provides a linear flight path, for example, ½ to 4 meters in length, and preferably about two meters in length. The ions are accelerated in two stages and the total acceleration is in the range of about 15,000–50,000 volts, positive or negative. The spectrometer is held under high vacuum, typically 10 uPa, which may be obtained, for example, after 2 minutes of introduction of the samples.

The face 19 of the disk 20 is struck with a laser beam to form the ions. Preferably the laser beam is from a solid laser. A suitable laser is an HY-400 Nd-YAG laser (available from Lumonics Inc., Kanata (Ottawa), Ontario, Canada), with a 2nd, 3rd and 4th harmonic generation/selection option. The laser is tuned and operated to produce maximum temporal and energy stability. Typically, the laser is operated with an output pulse width of 10 ns and an energy of 15 mj of UV per pulse. To improve the spatial homogeneity of the beam, the amplifier rod is removed from the laser.

The output of the laser is attenuated with a 935-5 variable attenuator (available from Newport Corp., Fountain Valley, Calif.), and focused onto the sample on the face 19, using a 12-in. focal length fused-slica lens. The incident angle of the laser beam, with respect to the normal of the disk's sample surface, is 70°. The spot illuminated on the disk is not circular, but a stripe of approximate dimensions 100×300 um or larger. The start time for the data system (i.e., the time the laser actually fired) is determined using a beam splitter and a P5-01 fast pyroelectric detector (available from Molectron Detector Inc., Campbell, Calif.). The laser is operated in the Q switched mode, internally triggering at 5 Hz, using the Pockels cell Q-switch to divide that frequency to a 2.5 Hz output.

The data system for recording the mass spectra produced is a combination of a TR8828D transient recorder and a 6010 CAMAC crate controller (both manufactured by Lecroy, Chestnut Ridge, N.Y.). The transient recorder has a selectable time resolution of 5–20 ns. Spectra may be accumulated for up to 256 laser shots in 131,000 channels, with the capability of running at up to 3 Hz, or with fewer channels up to 10 Hz. The data is read from the CAMAC crate using a Proteus IBM AT compatible computer. During the operation of the spectrometer, the spectra (shot-to-shot) may be readily observed on a 2465A 350 MHz oscilloscope (available from Tektronix, Inc., Beaverton, Oreg.). A suitable autosampler for mixing the matrix solution and each of the separated DNA samples and for depositing the mixture on a solid planar surface is the Model 738 Autosampler (available from Alcott Co., Norcoss, Ga.).

This linear TOF system may be switched from positive to negative ions easily, and both modes may be used to look at a single sample. The sample preparation was optimized for the production of homogeneous samples in order to produce similar signals from each DNA sample spot 18.

4. Data Analysis and Determination of Sequence

The raw data obtained from the laser desorption mass spectrometer 30 consists of ion current as a function of time after the laser pulse strikes the target containing the sample and matrix. This time delay corresponds to the "time-of-flight" required for an ion to travel from the point of formation in the ion source to the detector, and is proportional to the mass-to-charge ratio of the ion. By reference to results obtained for materials whose molecular weights are known, this time scale can be converted to mass with a precision of 0.01% or better.

Figure 3:
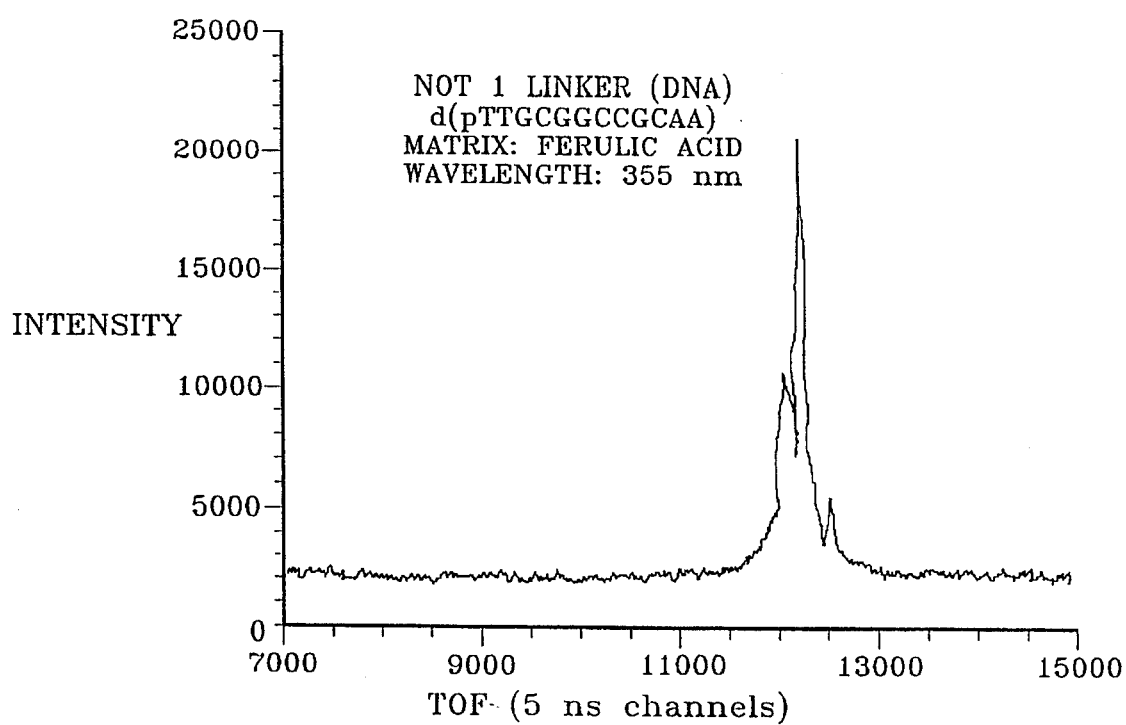
FIG. 3 is a mass spectrum of a DNA fragment obtained according to the present invention.

FIG. 3 is a graph of intensity v. time-of-flight of the pseudomolecularion region of a TOF mass spectrum of Not I Linker (DNA) in which the matrix is ferulic acid and the wavelength is 355 nm. Four consecutive spectra can be obtained using the present invention by the successive measurement of the four collections of DNA fragments obtained from fragmentation of each sample of DNA. Each of these spectra will correspond to the set of fragments ending in a particular base or bases G, G and A, C and T, or C. To determine the order of the peaks in the four spectra, a simple computer algorithm may be utilized.

It should be noted that the data obtained from the mass spectra contains significantly more useful information that the corresponding traces from electrophoresis. Not only can the mass order of the peaks be determined with good accuracy and precision, but also the absolute mass differences between adjacent peaks, both in individual spectra and between spectra, can be determined with high accuracy and precision. This information may be used to detect and correct sequence errors which might otherwise go undetected. For example, a common source of error which often occurs in conventional sequencing results from variations the amounts of the individual fragments present in a mixture due to variations in the cleavage chemistry. Because of this variation it is possible for a small peak to go undetected using conventional sequencing techniques. With the present invention, .such errors can be immediately detected by noting that the mass differences between detected peaks do not match the apparent sequence. In many cases, the error can be quickly corrected by calculating the apparent mass of the missing base from the observed mass differences across the gap. As a result, the present invention provides sequence data not only much faster than conventional techniques, but also data which is more accurate and reliable. This correction technique will reduce the number of extra runs which are required to establish the validity of the result.

What is claimed is:

1. Apparatus for sequencing DNA from different sets of DNA fragments, each set of DNA fragments having a common origin and terminating at a particular base along the unknown sequence, the apparatus comprising:

a plurality of samples, each including DNA fragments from a respective set of the DNA fragments and a matrix of light absorbent material;

a planar solid rotatable disk having a surface for supporting each of the plurality of samples when struck by the laser pulses;

a drive motor for rotating the rotatable disk;

laser beam means to strike each of the plurality of samples with a series of laser pulses to desorb ions of the DNA fragments in each of the plurality of samples;

mass spectrometer means to detect the mass weights of the ionized fragments, the mass spectrometer means including means for applying both a vacuum and an electric field within the mass spectrometer means; and computing means to determine the sequence of bases in the DNA fragments in response to the detected mass weights.

2. The apparatus as defined in claim 1, wherein the rotatable disk is mounted such that the laser pulses strike each of the plurality of samples at an acute angle with respect to a line perpendicular to the rotatable disk.

3. Apparatus for sequencing DNA from different sets of DNA fragments, each set of DNA fragments having a common origin and terminating at a particular base along the unknown sequence, comprising:

a planar solid rotatable disk having a surface;

means for rotating the disk;

a plurality of samples, each including DNA fragments from a respective set of the DNA fragments and matrix material supply means comprising a laser light absorbent material which forms a matrix with the DNA fragments, the plurality of samples being distributed on the surface of the rotatable disk;

laser beam means to strike each of the plurality of samples with a series of laser pulses to desorb ions of the DNA fragments in each of the plurality of samples;

mass spectrometer means to detect the mass weights of the ionized fragments, the mass spectrometer means including means for applying both a vacuum and an electric field within the mass spectrometer means; and computing means to determine the sequence of bases in the DNA fragments in response to the detected mass weights.

4. The apparatus as defined in claim 3, wherein the planar solid rotatable disk is mounted such that the laser pulses strike each of the plurality of samples at an acute angle with respect to a line perpendicular to the rotatable disk.

5. Apparatus for sequencing DNA, comprising:

a laser which emits a beam for striking samples of unlabeled, unseparated DNA with a series of laser pulses sufficient to desorb ions of the DNA;

a mass spectrometer for detecting mass weight of ionized DNA;

a sample transport means for providing the mass spectrometer with at least one sample;

an unlabeled, unseparated DNA mixed with a light absorbent material to form a solid matrix disposed on the sample transport means; and computing means to determine the sequence of bases in DNA in response to the detected mass weight.

6. The apparatus as defined in claim 5, further comprising:

a vacuum and an electric field within the mass spectrometer.

7. The apparatus as defined in claim 5, wherein the mass spectrometer is a time of flight mass spectrometer.

8. The apparatus as defined in claim 5, wherein the laser produces a laser beam wavelength in the range of from 260 to 560 nanometers.

9. The apparatus as defined in claim 5, wherein the sample transport means further comprises:

a planar solid surface for supporting DNA samples when struck by the laser pulses.

10. The apparatus as defined in claim 9, wherein:

the planar solid surface comprises a rotatable disk; and disk rotating means.

11. The apparatus as defined in claim 9, wherein the planar solid surface is mounted such that the laser pulses strike the DNA samples at an acute angle with respect to a line perpendicular to the planar solid surface.

12. The apparatus as defined in claim 5, wherein the mass spectrometer includes a plurality of charged plates for charging the ionized DNA at a potential of from 15,000 to 50,000 volts.

13. The apparatus as defined in claim 5, further comprising:

means for performing a plurality of base-specific reactions on DNA.

14. Apparatus for sequencing DNA, comprising:

samples of DNA, each including unlabeled, unseparated DNA fragments in combination with a matrix of light-absorbent material;

a laser which emits a beam for striking DNA samples with a series of laser pulses sufficient to desorb ions of said DNA fragments;

a mass spectrometer for detecting mass weights of said ionized DNA fragments, the mass spectrometer including a vacuum and an electric field; and computing means to determine the sequence of bases in the DNA fragments in response to the detected mass weights.

15. The apparatus as defined in claim 14, wherein the mass spectrometer is a time of flight mass spectrometer.

16. The apparatus as defined in claim 14, wherein the laser produces a laser beam wavelength in the range of from 260 to 560 nanometers.

17. The apparatus as defined in claim 14, further comprising:

a sample transport means for providing the mass spectrometer with at least one sample, the sample transport means having a planar solid surface for supporting DNA samples when struck by the laser pulses.

18. The apparatus as defined in claim 17, wherein a planar solid surface of the sample transport means has a precoated matrix thereon.

19. The apparatus as defined in claim 14, wherein the mass spectrometer includes a plurality of charged plates for charging the ionized DNA at a potential of from 15,000 to 50,000 volts.

20. The apparatus as defined in claim 14, further comprising:

means for performing a plurality of base-specific reactions on DNA.

* * * * *

UNITED STATES PATENT AND TRADEMARK OFFICE
CERTIFICATE OF CORRECTION

PATENT NO. : 5,453,247
DATED : September 26, 1995
INVENTOR(S) : Ronald C. Beavis, et al.

It is certified that error appears in the above-indentified patent and that said Letters Patent is hereby corrected as shown below:

On title page, item [63], "Related U.S. Application Data",
   delete "Oct. 7, 1992" and insert therefor --Nov. 13, 1992--.

Signed and Sealed this

Twenty-first Day of May, 1996

Attest:

BRUCE LEHMAN

*Attesting Officer*      Commissioner of Patents and Trademarks